United States Patent [19]

Baize

[11] Patent Number: 4,748,011

[45] Date of Patent: May 31, 1988

[54] METHOD AND APPARATUS FOR SWEETENING NATURAL GAS

[76] Inventor: Thomas H. Baize, P.O. Box 1007, Missouri City, Tex. 77459

[21] Appl. No.: 57,031

[22] Filed: Jun. 2, 1987

Related U.S. Application Data

[63] Continuation-in-part of Ser. No. 513,319, Jul. 13, 1983.

[51] Int. Cl.$^4$ .............................................. B01D 53/14
[52] U.S. Cl. ........................................ 423/228; 55/73; 55/174; 55/175; 423/234
[58] Field of Search ............... 55/32, 68, 73, 171–177; 423/226, 228, 234

[56] References Cited

U.S. PATENT DOCUMENTS

| | | | |
|---|---|---|---|
| 3,174,926 | 3/1965 | Walker et al. | 55/174 X |
| 3,331,188 | 7/1967 | Sinex | 55/174 X |
| 4,603,035 | 7/1986 | Connell et al. | 423/226 |

*Primary Examiner*—Charles Hart
*Attorney, Agent, or Firm*—Neal J. Mosely

[57] ABSTRACT

A method and apparatus are disclosed for sweetening of natural gas at the well head or at a common collection point from a number of wells, where, in the usual collection system for natural gas, the gas from one or more wells is collected through a collection line or manifold and often subjected to conventional treatments for dehydration and/or separation of petroleum condensates. A storage tank for sweetening liquid, comprising a solution of a low molecular weight aldehyde or ketone and water, methanol, isopropanol, and an amine buffer or inhibitor may be added. The resulting solution is connected by a conduit to a pump which is connected to an injector/atomizer extending laterally into the pipe at a point or points from the well head to sales line. The injector/atomizer sprays the sweetening liquid into the flowing stream of gas in an amount sufficient to react with the hydrogen sulfide to convert it into a hydroxymethyl (or other lower molecular weight hydroxyalkyl) mercaptan and other sulfur bearing compounds. The sweetening reaction takes place in-line without the need for a holding tank or reaction vessel. The reaction is complete and effective to completely sweeten a sour gas system.

7 Claims, 2 Drawing Sheets

METHOD AND APPARATUS FOR SWEETENING NATURAL GAS

BACKGROUND OF THE INVENTION

1. Field of the Invention

This invention relates to improvements in the sweetening of natural gas and more particularly to a method and apparatus for sweetening natural gas at the well head or a collection point in the field.

2. Brief Description of the Prior Art

The production of natural gas often requires the separation or removal of various contaminants from the gas before it can be sent on for use. Natural gas often includes a substantial amount of entrained water and vaporized liquid hydrocarbons, usually the more volatile ones. Consequently, the gas is subjected to treatment for separation of these components.

Natural gas may also contain gaseous impurities such as carbon dioxide and hydrogen sulfide which are acids in aqueous solution and thus corrosive. Hydrogen sulfide-containing gas is also highly toxic and malodorous and is referred to as "sour" gas. In fact, hydrogen sulfide is more toxic than HCN and presents the problem that it is highly malodorous at extremely low concentrations and tends to anesthetize the olefactory nerves with the result that a toxic exposure may not be recognized until it is too late. The removal or neutralization of hydrogen sulfide is therefore a matter of necessity from a safety standpoint.

The removal of carbon dioxide is not always required but can usually be removed by the other processes used to remove hydrogen sulfide. In many processes of treatment, the chemicals used for sweetening react with both carbon dioxide and hydrogen sulfide and therefore the total amount of these impurities is used in calculating the amount of treating chemicals needed.

In most procedures, the natural gas is first treated to remove water vapor and to separate condensable hydrocarbons or "condensate". The partial expansion of the gas through a choke to a lower pressure is effective to cool the gas sufficiently to remove both water and volatile hydrocarbons by condensing them from the gas stream. Often, there is a material added, such as ethylene glycol which will absorb or hydrate with the water to condense more readily from the gas stream. The expansion through the choke and consequent cooling is usually sufficient to condense the volatile liquid hydrocarbons which are recovered for use as solvents or fuel, i.e. casing head gasoline.

The major process for removal of acid constituents from natural gas is one using an alkanolamine, such as monoethanolamine (MEA), diethanolamine (DEA), and/or triethanolamine (TEA). Treatment with alkanolamines involves circulating natural gas upward through a treatment tower to contact the alkanolamines. The acid gases react with the alkanolamines to form either a hydrosulfite or a carbonate of an alkanolamine. The alkanolamines admixed with the reaction products are conducted to a stripping still where the alkanolamines are removed and returned to the treatment column. The reaction products are then conducted to a reactor where they are heated sufficiently to reverse the process and regenerate the alkanolamines and release the acid gases which may be flared to convert hydrogen sulfide to sulfur dioxide, or further reacted to a form for solid disposal, or sent to a sulfur manufacturing plant.

There are several variations on the alkanolamine desulfurization process in use. One such process is the Shell Sulfinol process (licensed by Shell) which utilizes a mixed solvent. The Sulfinol solvent is an admixture of sulfolane, water and di-isopropanolamine (DIPA). Another process of this type utilizes a mixture of alkanolamines with ethylene glycol and water. This process combines the removal of water vapor, carbon dioxide and hydrogen sulfide.

Another process for removal of hydrogen sulfide, uses a solid-gas chemical reaction. An iron sponge, consisting of a hydrated iron oxide on an inert support, is treated with the sour gas where the iron is converted to the sulfide. The iron sulfide can be reoxidized to the oxide with release of elemental sulfur.

Some physical processes are used for removal of carbon dioxide and hydrogen sulfide. Molecular sieves, i.e. zeolites and other materials having a pore size of molecular dimensions, which are specific in pore size for removal of carbon dioxide and hydrogen sulfide are used in the form of a bed through which the sour gas is passed. The bed is periodically regenerated by stripping with an inert gas. This process has the disadvantage present in most desulfurizing processes in that the separated hydrogen sulfide or sulfur dioxide must be disposed of in the field.

All of the above desulfurization process have the disadvantage that reaction vessels, strippers, stills, separators and the like must be provided, which have a high capital cost. Also, these processes have the disadvantage that the current laws dealing with air pollution make it difficult to dispose of the separated hydrogen sulfide or sulfur dioxide under field conditions.

The present invention involves the use of inexpensive equipment and reagents for sweetening which avoid the problem of disposal of separated hydrogen sulfide or sulfur dioxide under field conditions.

SUMMARY OF THE INVENTION

One of the objects of this invention is to provide a new and improved method and apparatus for sweetening sour natural gas at the well head or during collection.

Another object of this invention is to provide a method for sweetening sour natural gas at the well head or during collection which utilizes simple and inexpensive equipment.

Another object of this invention is to provide a system of simple and inexpensive equipment for injection of chemicals for sweetening sour natural gas at the well head or during collection under flowing conditions.

Still another object of this invention is to provide a method for sweetening sour natural gas at the well head or during collection which utilizes simple and inexpensive equipment for atomizing a sweetening solution into a flowing stream of natural gas.

Still another object of this invention is to provide a method for sweetening sour natural gas at the well head or during collection which utilizes simple and inexpensive equipment for atomizing a sweetening solution into a flowing stream of natural gas after separation of particulate impurities and removal of water and volatile hydrocarbons.

Yet another object of this invention is to provide a system of simple and inexpensive equipment for injecting or atomizing a chemical solution for sweetening sour natural gas at the well head or during collection under flowing conditions.

Yet another object of this invention is to provide a method for sweetening sour natural gas at the well head or during collection by injecting or atomizing a sweetening solution, comprising a mixture of a low molecular weight aldehyde or ketone and water, optionally including methanol, isopropanol and a buffer or inhibitor, singularly or in combination into a flowing stream of natural gas, and which utilizes simple and inexpensive equipment.

Another object of this invention is to provide a method for sweetening sour natural gas at the well head or during collection by injecting or atomizing a sweetening solution, comprising a solution of formaldehyde in methanol, isopropanol and a buffer or inhibitor, into a flowing stream of natural gas, and which utilizes simple and inexpensive equipment.

Other objects of this invention will become apparent from time to time throughout the specification and claims as hereinafter related.

These objects, and other objects of the invention are accomplished by the disclosed method and apparatus for sweetening of natural gas at the well head or at a common collection point from a number of wells, where, in the usual collection system for natural gas, the gas from one or more wells is collected through a collection line or manifold and subjected to a conventional treatment for dehydration and separation of petroleum condensate. A storage tank or barrel for a sweetening liquid, comprising a solution of a low molecular weight aldehyde or ketone and water with possibly methanol, and/or isopropanol, and/or an amine buffer or inhibitor, is connected by a conduit to a pump and then to an injector/atomizer extending laterally into the pipe at a point or points from the well head to sales. The injector/atomizer sprays the sweetening liquid into the flowing stream of gas in an amount sufficient to react with the hydrogen sulfide to convert it into a hydroxymethyl (or other lower molecular weight hydroxyalkyl) mercaptan and/or other sulfur compounds. The sweetening reaction takes place in-line without the need for a holding tank or reaction vessel. The reaction is complete and effective to completely sweeten the sour gas.

BRIEF DESCRIPTION OF THE DRAWINGS

FIG. 3 is a partially schematic diagram illustrating the injection of sweetening solution into the transfer gas line at any point or points from well head to sales in systems such as those shown in FIGS. 1 and 2, or the like.

DESCRIPTION OF THE PREFERRED EMBODIMENTS

This invention is based on the discovery that sour natural gas may be sweetened by injection of a sweetening solution into the produced gas line from well head through collection and separation systems. The sweetening solution is atomized into the flowing gas stream and reacts with the hydrogen sulfide in line to meet industry requirements. This sweetening method, and the apparatus used to carry it out, can be used with any conventional, i.e., prior art, system of apparatus for collection of natural gas and separation of condensate therefrom. The improved method and apparatus will be described below for use in two prior art systems of apparatus for collection of natural gas and separation of condensate therefrom. The two systems illustrated are ones which demonstrate the low temperature processes for separation of condensate from natural gas, either with or without glycol injection for inhibiting hydrate formation.

PRIOR ART SYSTEM FOR LOW TEMPERATURE SEPARATION OF NATURAL GAS FROM LIQUID CONDENSATE

Figure 1:
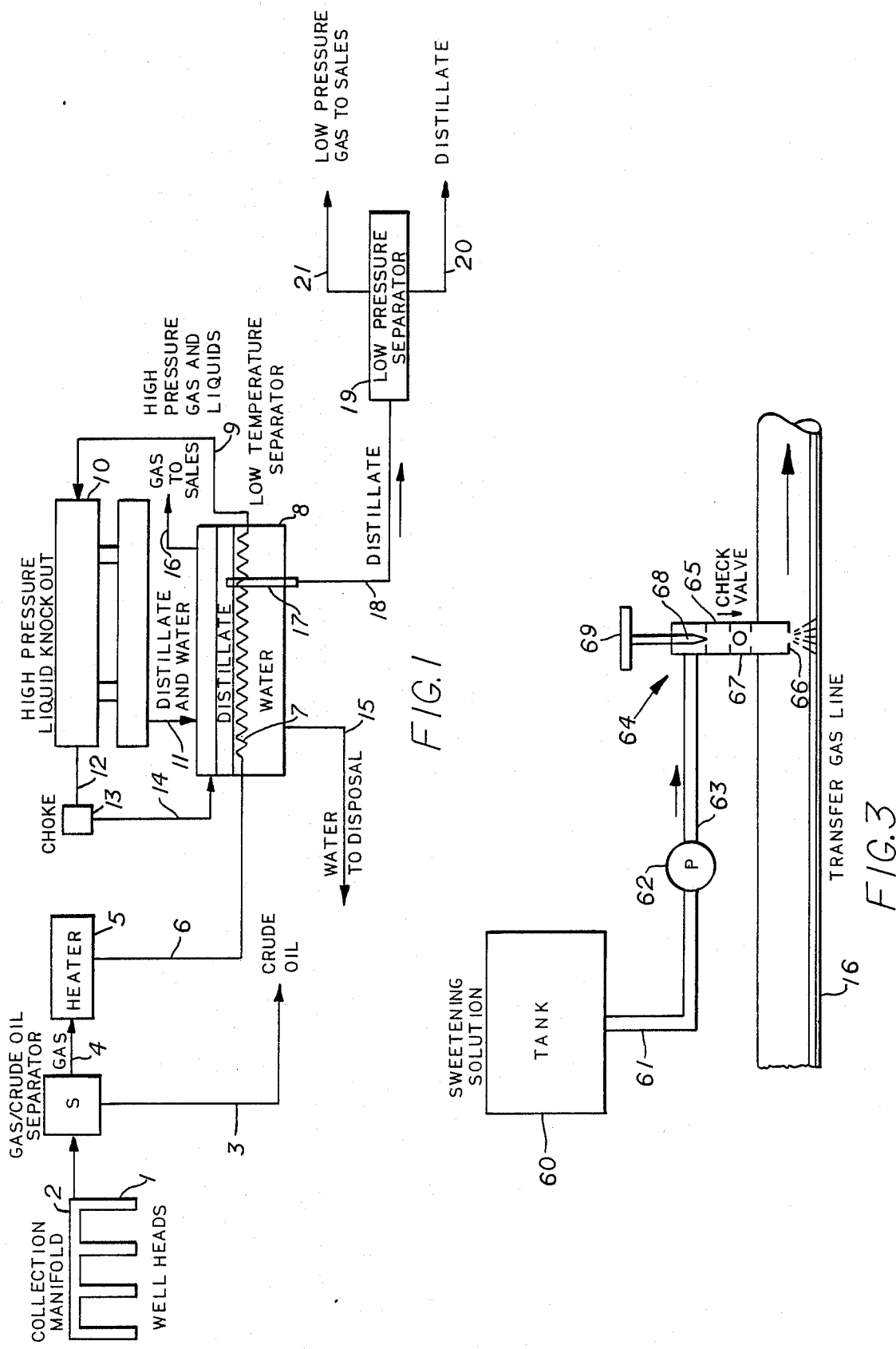
FIG. 1 is a schematic flow diagram illustrating a prior art system of apparatus for collection of natural gas and separation of condensate therefrom.

Referring to FIG. 1 of the drawings, there is shown a conventional, prior art, system for collection of natural gas and separation of liquid condensate therefrom.

Petroleum products are produced from a plurality of well heads 1 and collected through a collection manifold 2 as a mixture of natural gas, crude oil, entrained liquid condensate, water vapor, and often acid impurities, including carbon dioxide and hydrogen sulfide. As previously noted, natural gas containing hydrogen sulfide (sour gas) must be treated to remove hydrogen sulfide.

The petroleum mixture from manifold 2 passes through a separator S where the crude oil is removed through side line 3 to storage, transportation or further treatment. If the wells are producing only gas, the separator S may be omitted from the collection and treatment system. The gaseous portion of the well production, consisting of natural gas, entrained volatile liquid hydrocarbons (called "condensate"), and water vapor, is conducted by line 4 through a heater 5 to heat the mixture to provide heat in the separatory process equipment.

Line 6 conducts the heated gas through a heat exchange coil 7 in a low temperature separator 8 whose function will be described more thoroughly below. Line 9 conducts high pressure gas mixture from the separator 8 to the inlet side of a separator 10 known as a high pressure liquid knock out for removal of easily condensed and entrained liquids and vapors.

Line 11 conducts some condensed water and hydrocarbons (condensate) to low temperature separator 8. Outlet line 12 conducts high pressure gas to a choke 13 which is connected by line 14 to low temperature separator 8. Low temperature separator 8 separates the products into a bottom liquid layer of water, a top liquid layer of condensate, and a top volume of natural gas, essentially free of water and condensate.

Line 15 from the bottom of low temperature separator 8 conducts separated water to disposal. Line 16 at the top of low temperature separator 8 removes the separated natural gas for transportation to point of sale, i.e., the "sales gas" line. A stand pipe 17 in low temperature separator 8 removes condensed hydrocarbons (condensate) and some dissolved natural gas to line 18 connected to a low pressure separator 19. In the separator 19, the condensate is removed through bottom line 20 and the small amount of natural gas is removed through top line 21.

The system so far described contains the basic components for collection of natural gas and separation of water and distillate therefrom. The system, as shown, includes only one (the coil 7) of the many heat exchangers used in such a system, and does not include any means for desulfurization or sweetening or any means for inhibiting hydrate formation in the gas stream.

In the system shown, the separator S may be a conventional vertical oil and gas separator or the like. Heater 5 may burn part of the collected gas as fuel, or may use external fuel or even be electrically heated. The heated gas mixture passing through heat exchanger 7 keeps the water layer in low temperature separator 8 from freezing. High pressure liquid knock out is typically a double tube horizontal separator of conventional design with baffles which stop entrained liquid drops and cause them to drop into the lower part of the equipment to be conducted to the low temperature separator 8.

The gas mixture from high pressure liquid knock out 10 is substantially reduced in pressure by passing through choke 13 which cools the gas mixture sufficiently to cause the water and liquid hydrocarbons to condense out into separate layers in low temperature separator 8 where the natural gas, free or water and condensate, is removed to the sales gas line 16. The sales gas may still contain acid impurities such as hydrogen sulfide and/or carbon dioxide which must be removed. As previously noted these impurities may be removed by auxiliary treating apparatus which is very expensive.

PRIOR ART SYSTEM FOR LOW TEMPERATURE SEPARATION OF NATURAL GAS FROM LIQUID CONDENSATE INCLUDING GLYCOL INJECTION

Figure 2:
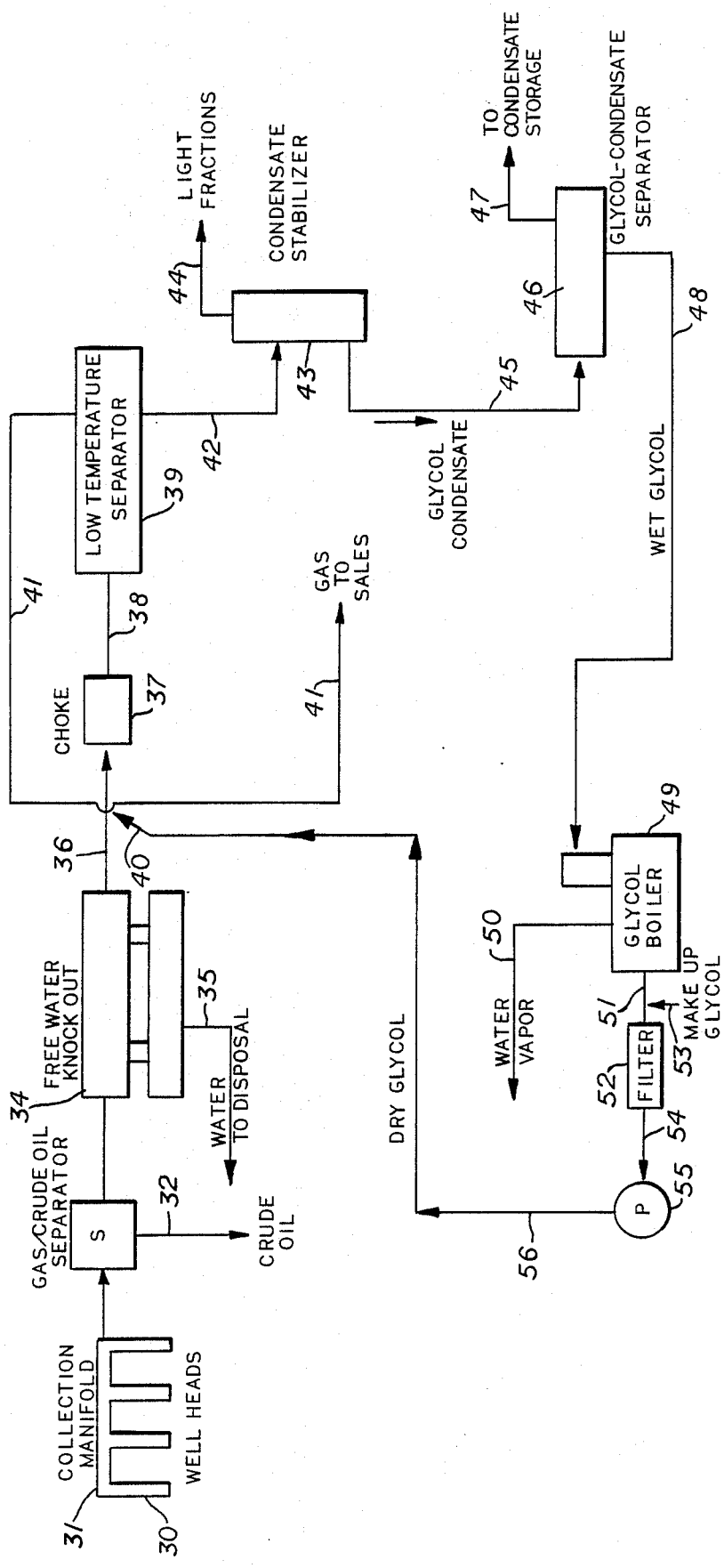
FIG. 2 is a schematic flow diagram illustrating a prior art system of apparatus for collection of natural gas and separation of condensate and water therefrom, including glycol injection and condensate stabilization.

Referring to FIG. 2 of the drawings, there is shown a conventional, prior art, system for collection of natural gas and separation of liquid condensate therefrom, including a system for glycol injection to assist in removal of water vapor and to prevent the formation of hydrate particles.

Petroleum products are produced from a plurality of well heads 30 and collected through a collection manifold 31 as a mixture of natural gas, crude oil, entrained liquid condensate, water vapor, and often acid impurities, including carbon dioxide and hydrogen sulfide. As previously noted, natural gas containing hydrogen sulfide (sour gas) must be treated to remove hydrogen sulfide. This is substantially as in FIG. 1.

The petroleum mixture from manifold 31 is conducted to separator S where the crude oil is removed through a side line 32 to storage, transportation or further treatment. If the wells are producing only gas, the separator S may be omitted from the collection and treatment system. The gaseous portion of the well production, consisting of natural gas, entrained volatile liquid hydrocarbons (called "condensate"), and water vapor, is conducted by line 33 to the inlet side of a separator 34 known as a free water liquid knock out for removal of water through line 35 for disposal.

Line 36 conducts high pressure gas to a choke 37 which is connected by line 38 to low temperature separator 39. Dry ethylene glycol is introduced into the gas stream by injector 40 ahead of choke 37. The glycol combines with the water vapor to inhibit formation of hydrates in the gas. This eliminates the need for the coil 7 in Fig. which was required to keep solid hydrates from forming. The glycol-water mixture separates from the natural gas in separator 39 and the glycol is subsequently dried and recycled.

Low temperature separator 39 separates the products into a layer of water-glycol and condensate, and a top volume of natural gas, essentially free of water and condensate. Line 41 at the top of low temperature separator 39 removes the separated natural gas for transportation to point of sale, i.e., the "sales gas" line.

The bottom outlet of low temperature separator 39 removes condensed hydrocarbons (condensate) and some dissolved natural gas to line 42 connected to a stabilizer (separator) column 43 where light fractions are removed overhead and collected through line 44. A mixture of wet glycol and condensate is removed through line 45 at the bottom of stabilizer 43 to a glycol-condensate separator 46. An overhead line 47 from separator 46 removes the condensate to storage.

Bottom line 48 from separator 46 conducts wet glycol to a drier or boiler 49 where water is removed through overhead line 50. Dried glycol is removed from boiler 49 through line 51 to the inlet side of filter 52. Make-up glycol is added, as needed, at addition port 53. Filter 52 is connected by line 54 to the inlet of pump 55, the outlet of which is connected by line 56 to glycol injector 40 as described above.

As was described in connection with FIG. 1, the system so far described contains the basic components for collection of natural gas and separation of water and distillate therefrom. The system, as shown, includes none of the many heat exchangers used in such a system, and does not include any means for desulfurization or sweetening or any means for inhibiting hydrate formation in the gas stream.

In the system shown, the separator S may be a conventional vertical oil and gas separator or the like. Free water knock out 34 is typically a double tube horizontal separator of conventional design with baffles which stop entrained water drops and cause them to drop into the lower part of the equipment to be conducted to water disposal.

The gas mixture from high pressure free water knock out 34 is mixed with glycol and then substantially reduced in pressure by passing through choke 37 which cools the gas mixture sufficiently to cause the water-glycol and liquid hydrocarbons to condense out in low temperature separator 39 where the natural gas, free or water and condensate, is removed to sales gas line 41. Sales gas may still contain acid impurities such as hydrogen sulfide and/or carbon dioxide which must be removed. As previously noted these impurities may be removed by auxiliary treating apparatus which is very expensive.

A PREFERRED EMBODIMENT OF THE METHOD AND APPARATUS FOR SWEETENING NATURAL GAS FLOWING IN THE SALES GAS LINE FROM THE GAS/CONDENSATE SEPARATION SYSTEM

In FIG. 3, there is shown a system of apparatus for introduction of a sweetening liquid into the flowing natural gas stream in the transfer gas line 16 (in FIG. 1) or at any point or points from well head or well heads to gas to sales 41.

The sweetening liquid is a solution comprising 10–50 % wt. of formaldehyde or other low molecular weight aldehyde, such as acetaldehyde, propionaldehyde, butyraldehyde, or the like, or a low molecular weight ketone, such as acetone, methyl ethyl ketone, diethyl ketone, methyl propyl ketone, or the like; 20–80% water; 10–50% methanol; 1–25% amine inhibitor; 0–5% sodium hydroxide or potassium hydroxide, and 2–5% isopropanol, where the percentage total one hundred, and at a pH 6.8–14. The amine inhibitors are water soluble oxidation and corrosion inhibitors including alkyl pyridines, quaternary ammonium salts, alkylamines, such as mono-, di-, and/or tri- methyl, ethyl, or propyl amines, alkanolamines, such as mono methanol, ethanol, or propanol amines, di- methanol, ethanol, or propanol amines, tri- methanol, ethanol, or propanol amines, dimethyl ethanol amine, methyl diethanol amine, dimethyl amino ethanol, or morpholine.

In FIG. 3, the system of apparatus comprises a drum or other storage tank 60 for the sweetening solution described above. Tank 60 is connected by line 61 to pump 62 which is in turn connected by line 63 to valve-injector 64 threaded into the wall of line 16 or other suitable point in the flow diagram shown in FIG. 2. Valve 64 has a body 65 with a spray nozzle or atomizer 66 at its end for atomizing the sweetening solution into the stream of flowing natural gas. Valve body 65 may have a check valve 67 permitting flow only into the gas line of FIG. 2 or FIG. 3. A shut off valve 68 operated by handle 69 may be present for shutting the valve and injector off during hook up or recharging the solution tank.

In operation, tank 60 is filled with a sweetening solution of 30% wt. formaldehyde; 30% water; 30% methanol; 5% imidazoline inhibitor; 2.0% sodium hydroxide and 3% isopropanol.

Shut off valve 68 is opened by handle 69 and pump 62 pumps the sweetening solution through injector 66 in a spray into point or points in the line of gas flow is the system as shown in FIGS. 2 and 3. The flowing gas is analyzed from time to time to determine the hydrogen sulfide content, and the flow of sweetening solution is adjusted to add an amount just sufficient for the reaction to convert the hydrogen sulfide to the hydroxymethyl mercaptan and other sulfur bearing compounds. Typically, 200–300 ppm of the sweetening solution per 100 ppm of hydrogen sulfide in the flowing natural gas stream injected into the flowing natural gas stream is effective to reduce the hydrogen sulfide level to 4.0 ppm or less, which meets both industry and environmental standards. Lower or higher concentrations of hydrogen sulfide are similarly treated.

While this invention has been described fully and completely with special emphasis on a few preferred embodiments, it should be understood that, within the scope of the appended claims, the invention may be practiced otherwise than as specifically described herein.

I claim:

1. In a method of collection and separation of natural gas wherein a sour natural gas from a well head is passed through a knock out separator to remove free liquids, the treated gas is expanded through a choke into a low temperature separator to cool the gas sufficiently to condense water or hydrocarbon condensate, or water and hydrocarbon condensate therein and to collect dry natural gas overhead therein, the steps which comprise removing dry gas continuously from said low temperature separator through a transfer line to a sales gas flow line, providing an injector-valve sealed in the wall of one of the flow lines in the system comprising a valve body with an atomizer nozzle extending into the stream of flowing dry natural gas, a check valve preventing back flow from the flow line, a shut off valve, and an inlet, providing a pump having an inlet and having an outlet connected to said valve inlet, providing a storage tank connected to said pump inlet, providing a sweetening solution in said tank consisting essentially of 10–50 % wt. a low molecular weight aldehyde, or a low molecular weight ketone; 20–80% water; 10–50% methanol; 1–25% amine inhibitor; 0–5% sodium hydroxide or potassium hydroxide and 2–5% isopropanol, where the percentages total one hundred, and the pH is 6.0–14 and operating said pump to supply said sweetening solution continuously at a rate sufficient to react continuously with hydrogen sulfide to sweeten the natural gas.

2. A method according to claim 1 in which said injector-valve comprises a tubular valve body threaded in the wall of said flow line having an inlet opening at the top and an atomizer nozzle at the end inside said flow line, a valve seat inside said valve body and a ball check valve positioned to close against said valve seat upon back flow therethrough, a second valve seat in said valve body, and a hand-operated valve member movable into engagement with said second valve seat to shut off flow during installation and removal of said pump and solution tank.

3. A method according to claim 1 in which said aldehyde or ketone is formaldehyde, acetaldehyde, propionaldehyde, butyraldehyde, acetone, methyl ethyl ketone, diethyl ketone, or methyl propyl ketone, and said amine inhibitors are water soluble oxidation and corrosion inhibitors comprising alkyl pyridines, quaternary ammonium salts, monomethylamine, monoethylamine, monopropylamine, dimethylamine, diethylamine, dipropylamine, trimethylamine, triethylamine, tripropylamine, monomethanolamine, monoethanolamine, monopropanolamine, dimethanolamine, diethanolamine, dipropanolamine, trimethanolamine, triethanolamine, tripropanolamine, dimethyl ethanol amine, methyl diethanol amine, dimethyl amino ethanol, imidazoline or morpholine.

4. A method according to claim 1 in which said sweetening solution is introduced typically in the amount of 200–300 ppm thereof per 100 ppm of hydrogen sulfide in the flowing natural gas stream gas stream to reduce the hydrogen sulfide level to 4.0 ppm or less. Lower or higher concentrations of hydrogen sulfide are similarly treated.

5. In an apparatus for collection and separation of natural gas which comprises means for collecting a sour natural gas from a well head, a knock out separator connected to receive said sour natural gas from said collection means and operable to remove entrained liquid droplets therefrom, a low temperature separator, a choke connected to receive said sour natural gas from said knock out separator and discharging into said low temperature separator to reduce the gas pressure to cool the gas sufficiently to condense water or hydrocarbon condensate, or water and hydrocarbon condensate therein and to collect dry natural gas overhead therein, and a sales gas flow line connected to remove dry natural gas continuously from said low temperature separator, the combination of sweetening apparatus therewith comprising an injector-valve sealed in the wall of said flow line comprising a valve body with an atomizer nozzle extending into the stream of flowing dry natural gas, a check valve preventing back flow from the flow line, a shut off valve, and an inlet, a pump having an inlet and having an outlet connected to said valve inlet, a storage tank connected to said pump inlet, and a sweetening solution in said tank consisting essentially of 10-50% wt. of a low molecular weight aldehyde, or a low molecular weight ketone; 20-80% water; 10-50% methanol; 1-25% amine inhibitor; 0-5% sodium hydroxide or potassium hydroxide and 2-5% isopropanol, where the percentages total one hundred, and at a pH of 6.8-14, whereby said pump may be operated to supply said sweetening solution continuously at a rate sufficient to react continuously with the hydrogen sulfide.

6. An apparatus according to claim 5 in which said injector-valve comprises a tubular valve body threaded in the wall of said flow line having an inlet opening at the top and an atomizer nozzle at the end inside said flow line, a valve seat inside said valve body and a ball check valve positioned to close against said valve seat upon back flow therethrough, a second valve seat in said valve body, and a hand-operated valve member movable into engagement with said second valve seat to shut off flow during installation and removal of said pump and solution tank.

7. A apparatus according to claim 5 in which said aldehyde or ketone is formaldehyde, acetaldehyde, propionaldehyde, butyraldehyde, acetone, methyl ethyl ketone, diethyl ketone, or methyl propyl ketone, and said amine inhibitors are water soluble oxidation and corrosion inhibitors comprising alkyl pyridines, quaternary ammonium salts, monomethylamine, monoethylamine, monopropylamine, dimethylamine, diethylamine, dipropylamine, trimethylamine, triethylamine, tripropylamine, monomethanolamine, monoethanolamine, monopropanolamine, dimethanolamine, diethanolamine, dipropanolamine, trimethanolamine, triethanolamine, tripropanolamine, dimethyl ethanol amine, methyl diethanol amine, dimethyl amino ethanol, imidazoline or morpholine.

* * * * *